United States Patent [19]

Pierce

[11] 4,085,281

[45] Apr. 18, 1978

[54] HEXAMETHYLENETETRAMINE PHENOXYLALKYL SALTS

[75] Inventor: James K. Pierce, Midland, Mich.

[73] Assignee: The Dow Chemical Company, Midland, Mich.

[21] Appl. No.: 753,754

[22] Filed: Dec. 23, 1976

[51] Int. Cl.$^2$ .......................................... C07D 295/02
[52] U.S. Cl. .................................................. 544/185
[58] Field of Search ...................... 260/248.5; 544/185

[56] References Cited

PUBLICATIONS

Jacobs et al., *J. Biological Chemistry*, vol. 21, pp. 439–453, (1915).

*Primary Examiner*—John M. Ford
*Attorney, Agent, or Firm*—Daniel L. DeJoseph; C. Kenneth Bjork

[57] ABSTRACT

3,5,7-Triaza-1-azoniatricyclo(3.3.1.1$^{3,7}$)-decane:1-(2-phenoxyethyl)-, bromides are disclosed. These compounds have utility as antimicrobials and herbicides.

5 Claims, No Drawings

HEXAMETHYLENETETRAMINE PHENOXYLALKYL SALTS

DESCRIPTION OF KNOWN PRIOR ART

Hexamethylenetetramine quaternary salts are known to be effective antimicrobial and fungicidal agents, as per the teachings of U.S. Pat. Nos. 3,268,399, 3,228,829 and 3,244,710.

SUMMARY OF THE INVENTION

The novel compounds of this invention are hexamethylenetetramine phenoxyalkyl salts of the formula

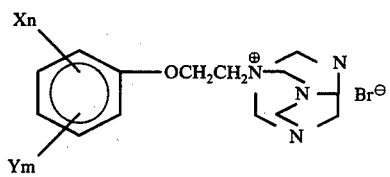

wherein
each X substituent independently represents F, Cl or Br;
each Y substituent independently represents H or a straight or branched chain alkyl group having from 1 to 4 carbon atoms;
$n$ is an integer with a value of from 1 to 5;
$m$ is an integer with a value of from 0 to 4; and
the sum of $n$ and $m$ is 5.

The novel compounds of the present invention are additionally herein referred to as the "active compounds".

The compounds of the present invention are prepared by the quaternization of hexamethylenetetramine by the corresponding phenoxyethyl bromides, which can be prepared according to the methods taught in J. Amer. Chem. Soc., 76, 585 (1954).

In preparing the compounds of the present invention, substantially one molar proportion of hexamethylenetetramine, in a solvent such as toluene or perchloroethylene, for example, is contacted with substantially equimolar proportions of the appropriate phenoxyethyl bromide. The mixture is refluxed for from about 10 to about 30 hours, and the precipitate is recovered by conventional separatory techniques such as filtration.

The following examples illustrate the present invention and the manner by which it can be practiced but as such should not be construed as limitations upon the overall scope of the same. The intermediate and product compounds are identified by elemental analysis and nuclear magnetic resonance spectroscopy.

EXAMPLE I

A mixture of 160.0 g (1.0 mole) 2,4-dichlorophenol, 235.0 g (1.26 mole) 1,2-dibromoethane, and 500 ml water were heated at reflux, during which time a solution of 42 g (1.05 mole) sodium hydroxide in 125 ml water was added to the mixture over a period of one hour. The solution was allowed to reflux for 10 hours, cooled and the organic layer distilled to give 176.0 g of 1-bromo-2-(2,4-dichlorophenoxy)ethane (b.p. 157°–160° C at 10 mm). A 15.0 g (0.055 mole) portion of this material was dissolved in 200 ml toluene and to this solution was added 7.8 g (0.055 mole) hexamethylene tetramine. The mixture was allowed to reflux for 24 hours. The precipitate was filtered, further purified by washing with ether, and air dried to give 18.1 g of a white powder identified as 3,5,7-triaza-1-azoniatricyclo(3.3.1.1$^{3,7}$)decane:1-(2-(2,4-dichlorophenoxy)ethyl)-, bromide (hereinafter referred to as Compound 1) m.p. 165°–169° C. The yield was calculated to be 79% from the phenoxyethyl bromide.

Analysis calculated for $C_{14}H_{19}BrCl_2N_4O$: C, 40.99; H, 4.16; N, 13.66 percent. Found: C, 40.93; H, 4.70; N, 13.75 percent.

Using similar procedures, the compounds of Examples II, III and IV (hereinafter referred to, respectively, as Compounds 2, 3 and 4) were prepared:

EXAMPLE II 3,5,7-Triaza-1-azoniatricyclo(3.3.1.1$^{3,7}$)-decane:1-(2-(4-chloro-2-methylphenoxy)ethyl)-, bromide. M.p. 180°–181° C.

Analysis calculated for $C_{15}H_{22}BrClN_4O$: C, 46.22; H, 5.69; N, 14.38 percent. Found: C, 46.67; H, 5.85; N, 16.15 percent.

EXAMPLE III 3,5,7-Triaza-1-azoniatricyclo(3.3.1.1$^{3,7}$)-decane:1-(2-(2-chloro-4-fluorophenoxy)ethyl)-, bromide. M.p. 170°–172° C.

Analysis calculated for $C_{14}H_{19}BrClFN_4O$: C, 42.71; H, 4.86; N, 14.23 percent. Found: C, 42.84; H, 4.80; N, 14.36 percent.

EXAMPLE IV 3,5,7-Triaza-1-azoniatricyclo(3.3.1.1$^{3,7}$)-decane:1-(2-(2,4,5-trichlorophenoxy)ethyl)-, bromide. M.p. 180°–182° C.

Analysis calculated for $C_{14}H_{18}BrCl_3N_4O$: C, 37.83; H, 4.08; N, 12.60 percent. Found: C, 37.17; H, 4.36; N, 14.03 percent.

The present invention's hexamethylenetetramine phenoxyalkyl salt compounds are useful as antimicrobial agents for the control of bacteria and fungi. This is not to suggest that these compounds and mixtures thereof with usual additives are equally effective against all such organisms at the same concentration. For such uses, these compounds can be employed in an unmodified form or in the form of a liquid or finely-divided solid compositions. Thus, the compounds can be dispersed in a finely-divided solid and employed as a dust. Such mixtures can also be dispersed in water with the aid of a surface-active agent and the resulting emulsion employed as a spray. In other procedures, the hexamethylenetetramine phenoxyalkyl salt compounds can be employed as the active constituents in solvent solutions, oil-in-water or water-in-oil emulsions. The augmented compositions are adapted to be formulated as concentrates and subsequently diluted with additional liquid or solid adjuvants to produce the ultimate treating compositions. Good results are obtained when employing compositions containing antimicrobial concentrations and usually from about 50 to about 500 parts by weight of one or more of the active compounds per million parts of such compositions.

In representative activity tests, Compounds 1, 2, 3 and 4 were separately dispersed in warm melted nutrient agar which was then poured into Petri dishes and allowed to solidify, the compounds being employed in an amount sufficient to provide from 10 to 500 parts by weight thereof per million parts (ppm) of the ultimate agar composition. The surface of the agar was then inoculated with a variety of bacterial and fungal pest organisms, and the inoculated plates were incubated under conditions conducive to bacterial and fungal growth. Similar check plates in which the agar contains no active hexamethylenetetramine phenoxyalkyl salt compounds or other toxic compounds were similarly inoculated and incubated.

In such operations, Compounds 1, 2, 3 and 4 gave 100% growth inhibition (kills) and control of the following organisms at the indicated concentrations in parts per million:

TABLE I

Antimicrobial Activity

| Organism | Compound (Concentration in ppm) | | | |
|---|---|---|---|---|
| | I | II | III | IV |
| *Staphyloccus aureus* | 500 | 50 | 50 | 50 |
| *Salmonella typhi* | 100 | 50 | 50 | 10 |
| *Enterobacter aerogenes* | 500 | 50 | 50 | 50 |
| *Pseudomonas aeruginosa* (PRD-10) | 500 | 50 | 50 | 50 |
| *Bacillus subtilis* | 500 | 50 | 50 | 50 |
| *Escherichia coli* | 500 | 50 | 50 | 50 |
| *Candida pelliculosa* | 500 | 500 | 500 | — |
| *Ceratocystis ips* | 500 | — | — | 500 |
| *Trichophyton mentagrophytes* | 100 | 50 | 50 | 50 |
| *Aspergillus niger* | — | 500 | 500 | 500 |

The compounds of the present invention have also displayed herbicidal activity. For example, Compounds 1, 2, 3 and 4 were separately tested in post-emergent herbicide operations against a variety of potentially undesirable plants by contacting said plants with compositions that contained an active compound at a concentration of 4,000 parts by weight of the compound per million parts by weight of the ultimate dispersion. Table II indicates the percent kill of the treated plants when compared with untreated plants.

TABLE II

Post-Emergent Herbicide Activity
Percent Kill at 4,000 PPM

| Plant | Compound | | | |
|---|---|---|---|---|
| | I | II | III | IV |
| Pigweeds | 100 | 100 | 100 | 80 |
| Cotton | 55 | 0 | 30 | 30 |
| Crabgrass | 0 | 0 | 35 | 70 |
| Bindweed | 75 | — | — | — |
| Sorghum | 30 | — | — | — |
| Barnyard Grass | 65 | 35 | 65 | 0 |
| Beans | 45 | — | — | — |
| Wild Oats | 30 | 0 | 60 | 0 |
| Yellow Foxtail | 85 | 0 | 40 | 40 |
| Velvet Leaf | 60 | 0 | 100 | 60 |

What is claimed is:

1. A compound selected from the group consisting of 3,5,7-triaza-1-azoniatricyclo(3.3.1.1$^{3,7}$)-decane:1-(2-(2,4-dichlorophenoxy)ethyl)-, bromide; 3,5,7-triaza-1-azoniatricyclo(3.3.1.1$^{3,7}$)decane:1-(2-(4-chloro-2-methylphenoxy)ethyl)-, bromide; 3,5,7-triaza-1-azoniatricyclo(3.3.1.1$^{3,7}$)decane:1-(2-(2-chloro-4-fluorophenoxy)ethyl)-, bromide; and 3,5,7-triaza-1-azoniatricyclo(3.3.1.1$^{3,7}$)decane:1(2-(2,4,5-trichlorophenoxy)ethyl)-, bromide.

2. The compound of claim 1 which is 3,5,7-triaza-1-azoniatricyclo(3.3.1.1$^{3,7}$)decane:1-(2-(2,4-dichlorophenoxy)ethyl)-, bromide.

3. The compound of claim 1 which is 3,5,7-triaza-1-azoniatricyclo(3.3.1.1$^{3,7}$)decane:1-(2-(4-chloro-2-methylphenoxy)ethyl)-, bromide.

4. The compound of claim 1 which is 3,5,7-triaza-1-azoniatricyclo(3.3.1.1$^{3,7}$)decane:1-(2-(2-chloro-4-fluorophenoxy)ethyl)-, bromide.

5. The compound of claim 1 which is 3,5,7-triaza-1-azoniatricyclo(3.3.1.1$^{3,7}$)decane:1-(2-(2,4,5-trichlorophenoxy)ethyl)-, bromide.

* * * * *

UNITED STATES PATENT AND TRADEMARK OFFICE
CERTIFICATE OF CORRECTION

PATENT NO. : 4,085,281
DATED : April 18, 1978
INVENTOR(S) : James K. Pierce

It is certified that error appears in the above-identified patent and that said Letters Patent are hereby corrected as shown below:

Title Page, "Title" line 2 "PHENOXYLALKYL" should read --PHENOXYALKYL--;

Column 1, line 2, "PHENOXYLALKYL" should read --PHENOXYALKYL--;

Signed and Sealed this

Tenth Day of October 1978

[SEAL]

Attest:

RUTH C. MASON
Attesting Officer

DONALD W. BANNER
Commissioner of Patents and Trademarks